(12) United States Patent
Boone et al.

(10) Patent No.: US 7,255,671 B2
(45) Date of Patent: Aug. 14, 2007

(54) INFANT CARE APPARATUS

(75) Inventors: Otho N. Boone, Ambler, PA (US); Patricia S. Maher, Alpharetta, GA (US); Ian McDermott, Lincoln University, PA (US); Nancy St. Clair, Malvern, PA (US)

(73) Assignee: Draeger Medical Infant Care, Inc., Telford, PA (US)

( * ) Notice: Subject to any disclaimer, the term of this patent is extended or adjusted under 35 U.S.C. 154(b) by 475 days.

(21) Appl. No.: 10/490,773

(22) PCT Filed: Oct. 3, 2002

(86) PCT No.: PCT/US02/31406

§ 371 (c)(1),
(2), (4) Date: Mar. 25, 2004

(87) PCT Pub. No.: WO03/030801

PCT Pub. Date: Apr. 17, 2003

(65) Prior Publication Data

US 2004/0236174 A1 Nov. 25, 2004

Related U.S. Application Data

(60) Provisional application No. 60/327,496, filed on Oct. 5, 2001, provisional application No. 60/373,479, filed on Apr. 18, 2002.

(51) Int. Cl.
*A61G 11/00* (2006.01)
(52) U.S. Cl. .......................... 600/22; 600/21
(58) Field of Classification Search ............ 600/21–22, 600/300; 128/845–846, 205.26, 897; 5/603, 5/620, 81.1, 655
See application file for complete search history.

(56) References Cited

U.S. PATENT DOCUMENTS

| 2,663,608 | A | | 12/1953 | Schauer |
| 3,470,866 | A | * | 10/1969 | Gittelson ...................... 600/22 |
| 5,308,310 | A | * | 5/1994 | Roff et al. .................... 600/21 |
| 5,453,077 | A | | 9/1995 | Donnelly et al. |
| 5,515,865 | A | * | 5/1996 | Scanlon ...................... 600/534 |
| 5,759,149 | A | | 6/1998 | Goldberg et al. |
| 6,011,477 | A | * | 1/2000 | Teodorescu et al. ..... 340/573.1 |

(Continued)

FOREIGN PATENT DOCUMENTS

DE 73 34 435.1 1/1974

(Continued)

*Primary Examiner*—Charles A. Marmor, II
*Assistant Examiner*—Christine D. Hopkins
(74) *Attorney, Agent, or Firm*—Caesar, Rivise, Bernstein, Cohen & Pokotilow, Ltd.

(57) ABSTRACT

A patient care apparatus comprises a portable patient support module having a first mattress, a first platform carrying the first mattress, and a first canopy positioned on the first platform to enclose an infant positioned on the first mattress in a first isolation chamber. The portable patient support module is configured to be carried by hand when the infant is positioned on the first mattress. The patient care apparatus further comprises a second patient support module having a second mattress, a second platform carrying the second mattress, and a second canopy positioned on the second platform. The second platform and the second canopy cooperate to enclose the portable patient support module positioned on the second mattress in a second isolation chamber.

15 Claims, 7 Drawing Sheets

U.S. PATENT DOCUMENTS

| | | |
|---|---|---|
| 6,210,320 B1 | 4/2001 | Rogone et al. |
| 6,253,380 B1 * | 7/2001 | Larsson et al. .................. 2/114 |
| 6,367,476 B1 | 4/2002 | Conn |
| 6,375,017 B1 | 4/2002 | Schattner et al. |
| 6,409,654 B1 * | 6/2002 | McClain ....................... 600/22 |
| 6,577,893 B1 * | 6/2003 | Besson et al. ............... 600/509 |
| 2001/0035702 A1 | 11/2001 | Murphy et al. |

FOREIGN PATENT DOCUMENTS

| | | |
|---|---|---|
| DE | 24 33 882 | 2/1976 |
| DE | 32 05 097 A1 | 10/1982 |
| DE | 39 15 882 A1 | 11/1990 |
| DE | 42 28 873 C1 | 10/1993 |
| DE | 297 09 848 U1 | 10/1997 |
| WO | WO 99/12511 A1 | 3/1999 |
| WO | WO 00/69387 A1 | 11/2000 |

* cited by examiner

INFANT CARE APPARATUS

CROSS-REFERENCE TO RELATED APPLICATIONS

This application is a U.S. national counterpart application of international application Ser. No. PCT/US02/31406 filed Oct. 3, 2002, which claims the benefit of U.S. provisional applications Ser. Nos. 60/327,496 and 60/373,479 filed Oct. 5, 2001, and Apr. 18, 2002, respectively.

BACKGROUND OF THE INVENTION

The present disclosure relates to patient care apparatus, and particularly to apparatus for caring for infants. More particularly, the present disclosure relates to incubators for caring for infants.

Patient care apparatus, such as incubators, are used to provide a controlled environment for infants. Premature infants may require an extended stay in a hospital in which case they may, on occasion, need to be transported between locations in the hospital for testing or other health care procedures. It is desirable to be able to transport the premature infants readily in the hospital while maintaining a controlled environment for the premature infants.

SUMMARY OF THE INVENTION

According to the present disclosure, a patient care apparatus comprises a portable patient support module having a first mattress, a first platform carrying the first mattress, and a first canopy positioned on the first platform to enclose an infant positioned on the first mattress in a first isolation chamber. The portable patient support module is configured to be carried by hand when the infant is positioned on the first mattress. The patient care apparatus further comprises a second patient support module having a second mattress, a second platform carrying the second mattress, and a second canopy positioned on the second platform. The second platform and the second canopy cooperate to enclose the portable patient support module positioned on the second mattress in a second isolation chamber.

According to an aspect of the disclosure, the portable patient support module has a sensor for sensing a physiologic condition of the infant and circuitry coupled to the sensor. The circuitry is carried by the first platform beneath the first mattress and has a transmitter for wirelessly sending data relating to the physiologic condition sensed by the sensor. A portable monitor is provided for wirelessly receiving the data sent by the transmitter.

According to another aspect of the disclosure, the first canopy has a bottom edge resting on the first platform. The first platform has a groove cooperating with the bottom edge of the first canopy to provide a passage for receiving a line associated with care of the infant.

According to another aspect of the disclosure, the first platform has a rail. A line clip for receiving a line associated with care of the infant is coupled to the rail for movement along the rail.

According to another aspect of the disclosure, the first canopy has an aperture. A line extends into the aperture to introduce an environmentally controlled fluid into the first isolation chamber for the infant positioned on the first mattress.

According to another aspect of the disclosure, the first platform has an opening for receiving an x-ray tray underneath the first platform allowing an x-ray to be taken of the infant while the infant is positioned on the first mattress.

Additional aspects of the disclosure will become apparent to those skilled in the art upon consideration of the following detailed description of illustrative embodiments exemplifying the best mode as presently perceived.

BRIEF DESCRIPTION OF THE DRAWINGS

The detailed description particularly refers to the accompanying figures in which.

DETAILED DESCRIPTION OF THE DRAWINGS

Figures 1, 2:
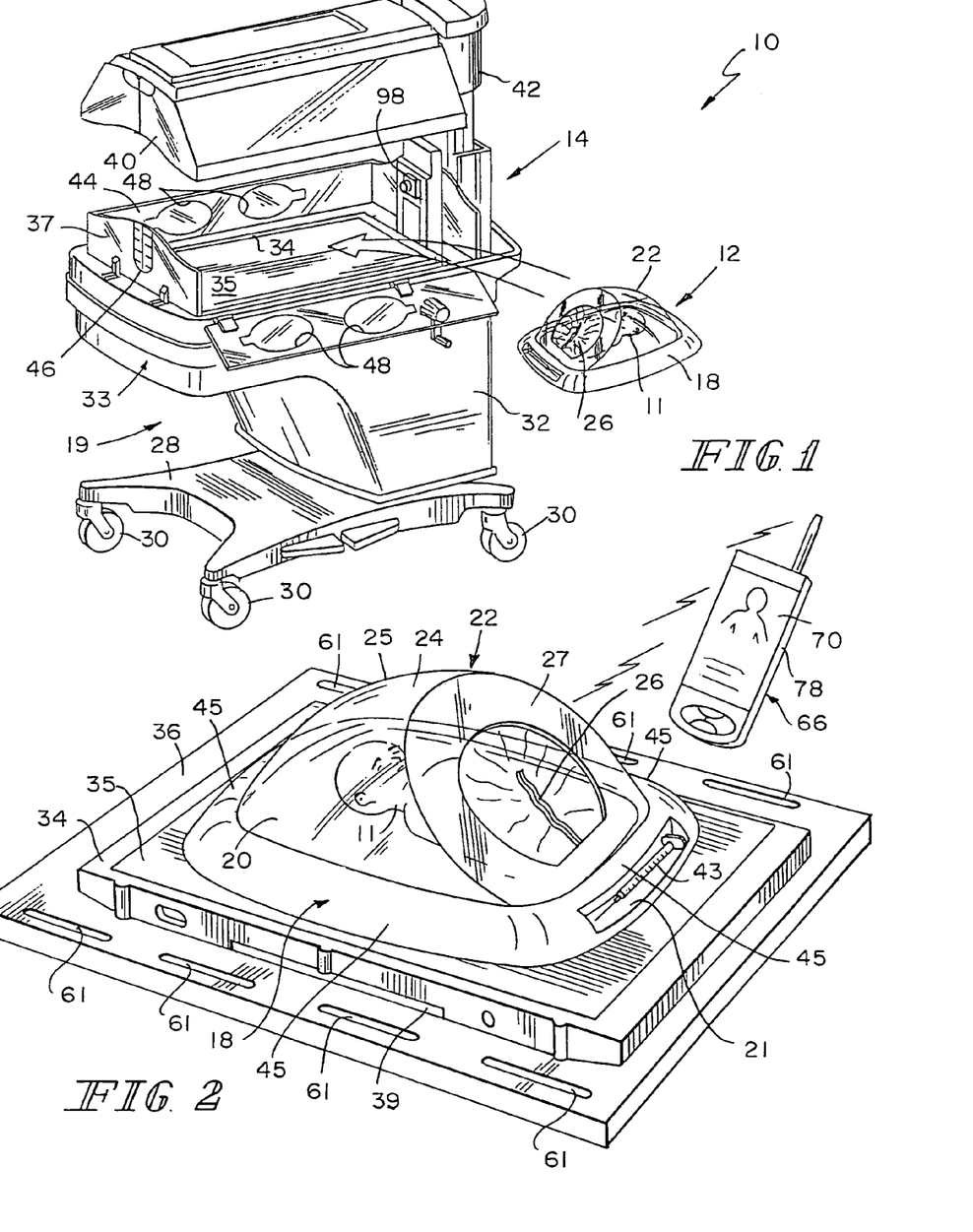
FIG. 1 is a perspective view of a patient care apparatus having a patient support module shown as an incubator with an open canopy to receive a portable patient support module carrying an infant therein.
FIG. 2 is a perspective view of the portable patient support module of FIG. 1 in wireless communication with a portable device for monitoring the condition of the infant in the portable patient support module.

A patient care apparatus 10 illustrated in FIG. 1 is configured to provide a controlled environment for an infant 11, such as one born prematurely. Apparatus 10 has a portable patient support module 12 and an incubator or second patient support module 14 for receiving portable module 12 with infant 11 positioned within portable module 12. Portable module 12 is configured to be carried by hand so that infant 11 can be transported away from incubator 14 to provide, for example, health care services to infant 11. Although module 12 is discussed herein as being used in conjunction with incubator 14, module 12 may be used with other patient care modules 14, such as bassinettes, radiant warmers, and the like. In addition, module 12 may be transported on movable carts, stretchers, hospital beds, and the like, rather than being carried by hand.

Incubator 14 has a platform 19 having a base 28 with casters 30 mounted thereto and a pedestal 32 extending upwardly from base 28 and supporting a tub 33 of platform 19, as illustrated in FIG. 1. A plate 34 of platform 19 carries a mattress 35 and provides a space for an x-ray tray 39, as illustrated in FIG. 2. Plate 34 is positioned on a panel 36 of tub 33. Platform 19 further has a walled portion 37 mounted on tub 33. A canopy 40 is mounted on a lift arm 42 for vertical movement of canopy 40 between an opened position away from portion 37 and a closed position engaging portion 37 to provide an enclosed infant isolation chamber 44 for isolating infant 11. Incubator 14 is sized so that infant 11 can be positioned in chamber 44 with or without portable module 12. That is, infant 11 can be placed directly on mattress 35 or placed in portable module 12 which is placed on mattress 35. Portion 37 has a grommet 46 for line pass-through and access ports 48 so that a caregiver can access infant 11 positioned in chamber 44 directly on mattress 35 or in portable module 12. Heated and/or humidified air is generated in tub 33 and forced through vents 61 (FIG. 2) of panel 36 to control temperature and humidity levels in isolation chamber 44.

Figure 4:
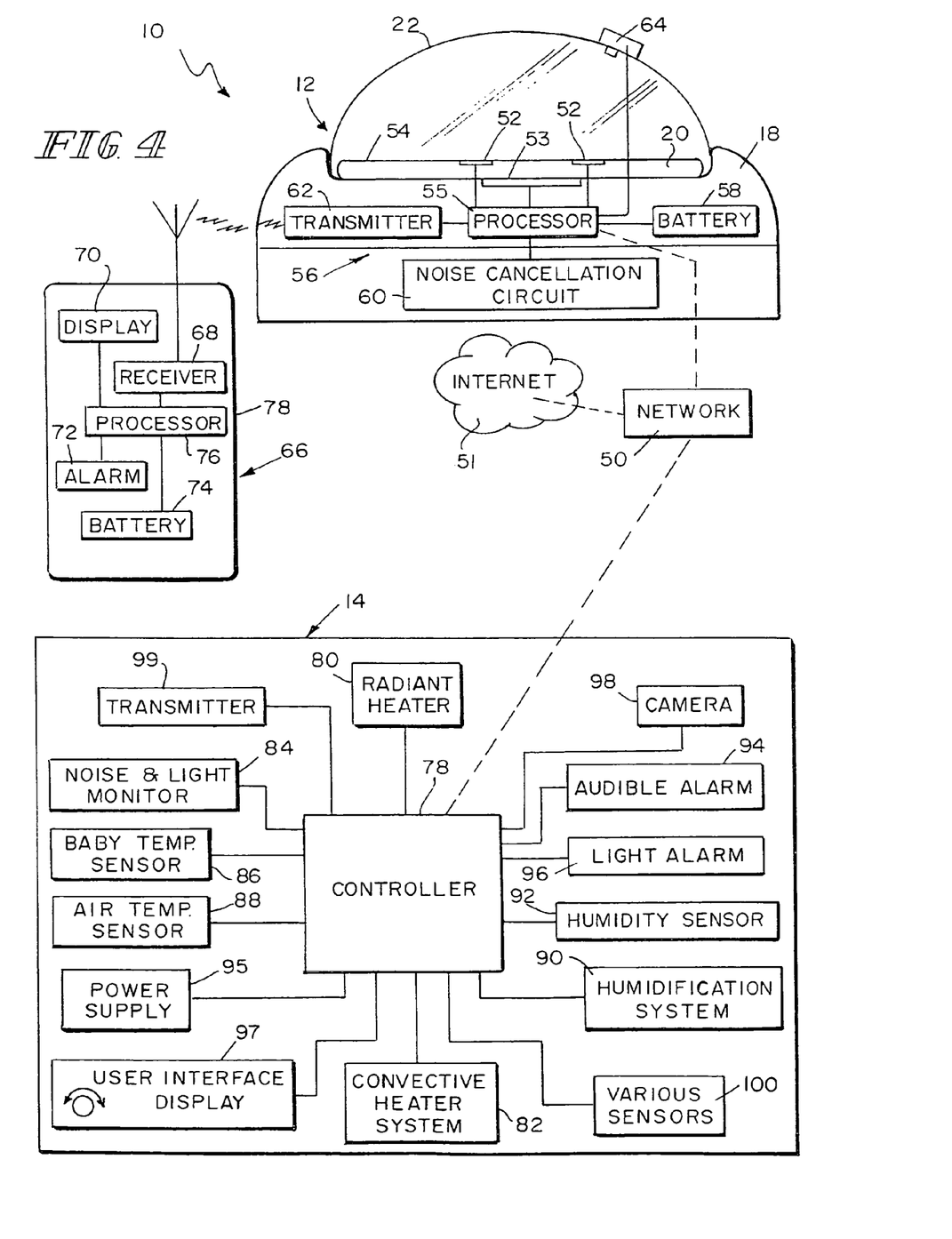
FIG. 4 is a diagrammatic view of the patient care apparatus of FIG. 1 showing the portable patient support module in communication with a controller of the incubator over a communication network adapted to communicate with the Internet.

Incubator 14 has a controller 78 for controlling operation of incubator 14, as illustrated in FIG. 4. Incubator 14 has a variety of infant care systems coupled to controller 78 for regulating the environment in isolation chamber 44. Such infant care systems include a radiant heater 80, a convective heater system 82, a noise and light monitor 84, an infant temperature sensor 86, an air temperature sensor 88, a humidification system 90, a humidity sensor 92, an audible alarm 94, a light alarm 96, a camera 98, a transmitter 99, and various other sensors 100. Incubator 14 further has a power supply 95 and a user interface display 97. U.S. Pat. Nos. 5,759,149 and 5,453,077 are hereby incorporated by reference herein to provide further details of the various systems of incubator 14.

Figure 3:
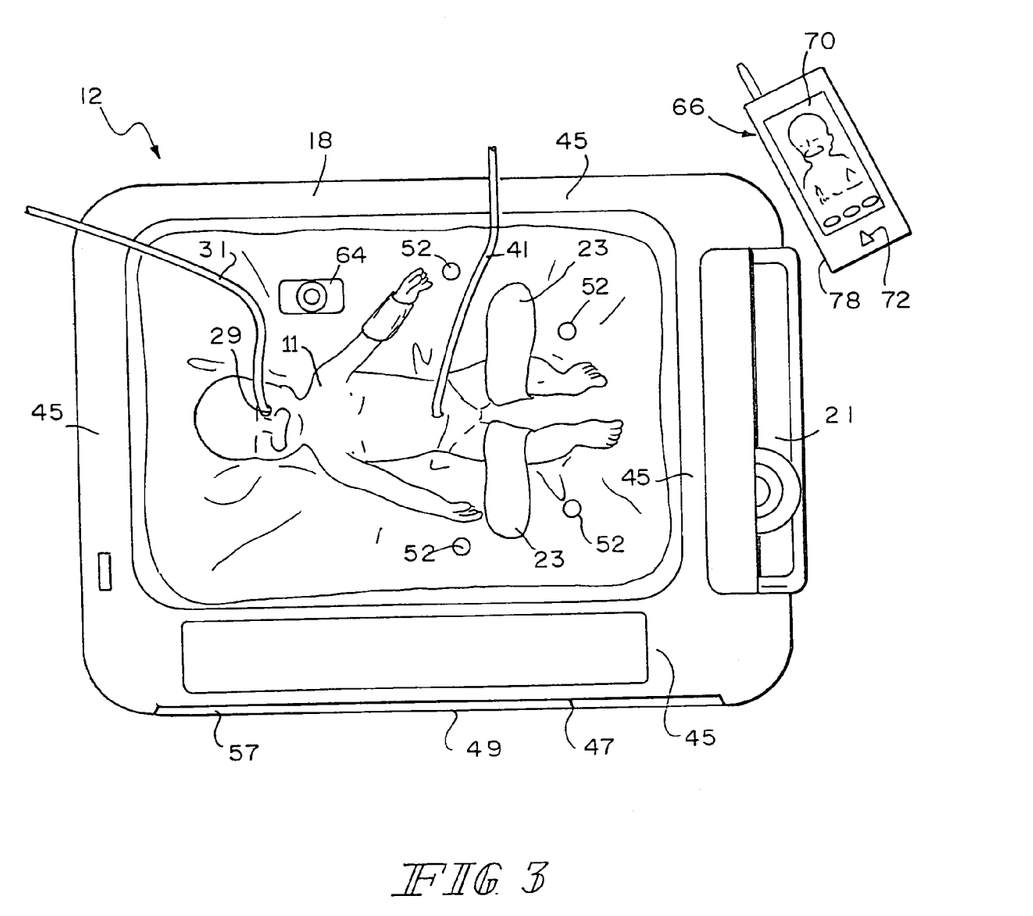
FIG. 3 is a top plan view of the portable patient support module and portable device of FIG. 2.

Portable module 12 has a carrying platform 18, a deformable, heat- and light-transmitting mattress 20 positioned on and carried by platform 18, and a removable canopy 22 positioned on and carried by platform 18, as illustrated in FIGS. 1-3. When canopy 22 is positioned on platform 18, canopy 22 and platform 18 cooperate to provide an enclosed infant isolation chamber 24 (FIG. 2) for isolating infant 11 positioned on mattress 20. The caregiver can carry portable module 12 with infant 11 positioned on mattress 20 in chamber 24 by holding onto platform 18. Leg restraint straps 23 (FIG. 3) coupled to mattress 20 are provided to restrict movement of infant 11. One of sides 45 of platform 18 has a tray 21 (FIGS. 2-3) for holding one or more items, such as a syringe 43. In one embodiment (FIG. 3) of platform 18, one of sides 45 has a notch 47 providing an opening 57 for receiving an x-ray tray 49 or a cassette of x-ray film. In another embodiment (FIG. 2) of platform 18, none of sides 45 has notch 47 for x-ray tray 49.

Canopy 22 is made of generally transparent material allowing a caregiver to see infant 11 positioned in chamber 24 on mattress 20. The caregiver can access infant 11 through a grommet 26 (FIGS. 1-2) of canopy 22 or by lifting canopy 22 off platform 18. Canopy 22 has a domal portion 25 and an upwardly inclined annular planar portion 27 coupled to domal portion 25, as illustrated in FIG. 2. Grommet 26 is coupled to and surrounded by planar portion 27. Domal portion 25 has an aperture 29 (FIG. 3) for receiving an infant care line, for example, a feeding line 31, extending into chamber 24. Portable module 12 is configured to receive one or more other infant care lines 41 extending into chamber 24.

Portable module 12 has sensors 52 embedded in a top surface 54 of mattress 20 for sensing one or more physiologic conditions of infant 11 lying on mattress 20, as illustrated in FIG. 4. Sensors 52 are configured to sense physiologic conditions such as respiratory rate and heart rate of infant 11. In some embodiments, one of sensors 52 is configured to sense blood pressure with the aid of an attachment (not shown) connected to infant 11. Portable module 12 also has a light source 53 coupled to platform 18 below mattress 20 to provide phototherapy to infant 11. Sensors 52 and light source 53 are coupled to a processor 55 of circuitry 56 which is carried by platform 18 beneath mattress 20. Circuitry 56 further has a battery 58 for powering processor 55, a noise cancellation circuit 60 coupled to processor 55 for canceling sound waves that might disturb infant 11, and a transmitter 62 coupled to processor 55 for wirelessly sending data relating to the physiologic conditions sensed by sensors 52 and other data relating to infant 11 such as, for example, the name of infant 11, her likes and dislikes, and her age and attending nurse. A camera 64 coupled to processor 55 is mounted to canopy 22 allowing camera 64 to obtain photo images of infant 11 positioned on mattress 54.

A portable monitor 66 (FIGS. 2-4) for remotely monitoring infant 11 positioned in chamber 24 has a receiver 68 for wirelessly receiving the data sent by transmitter 62. Monitor 66 also has a display 70 for displaying the data to a caregiver who may be positioned at a location remote from portable module 12. Monitor 66 further has an alarm 72 (for example, a visual alarm, an auditory alarm, and/or a vibratory alarm) for alerting the caregiver of a condition of infant 11 and a battery 74 for powering monitor 66. A processor 76 of monitor 66 is coupled to receiver 68, display 70, alarm 72, and battery 74 to control operation of monitor 66. Monitor 66 has a housing 78 containing receiver 68, display 70, alarm 72, battery 74, and processor 76. Housing 78 is sized so that monitor 66 can be held by a hand of the caregiver. In some embodiments, display 70 includes a liquid crystal display (not shown) for displaying information to the care giver.

Portable module 12 and incubator 14 are configured to communicate with one another over a communication network 50, such as the central communication network of a hospital, as illustrated in FIG. 4. Processor 55 of portable module 12 is couplable to network 50 by a data port in one area of the hospital and controller 78 of incubator 14 is couplable to network 50 by a data port in another area of the hospital. Network 50 is in turn couplable to the Internet 51 to permit a caregiver to monitor infant 11 when infant 11 is positioned within either, or both, of portable module 12 and incubator 14. In some embodiments, data is transmitted from one or both of modules 12, 14 to monitor 66 via network 50. In such embodiments, network 50 has transmitters and receivers located throughout the healthcare facility and monitor 66 has a transmitter that emits a signal either periodically or when prompted by network 50 so that network 50 is able to track the location of monitor 66 and send data to monitor 66.

A portable patient support module 112 (FIGS. 5-11) is similar to module 12 except as otherwise noted. Portable module 112 has a carrying platform 118, deformable, heat- and light-transmitting mattress 20 positioned on and carried by platform 118, and removable canopy 22 positioned on and carried by platform 118. When canopy 22 is positioned on platform 118, canopy 22 and platform 118 cooperate to provide an enclosed infant isolation chamber 24 for isolating infant 11 positioned on mattress 20. The caregiver can carry portable module 112 by hand with infant 11 positioned in chamber 24 by holding onto platform 118.

Figure 5:
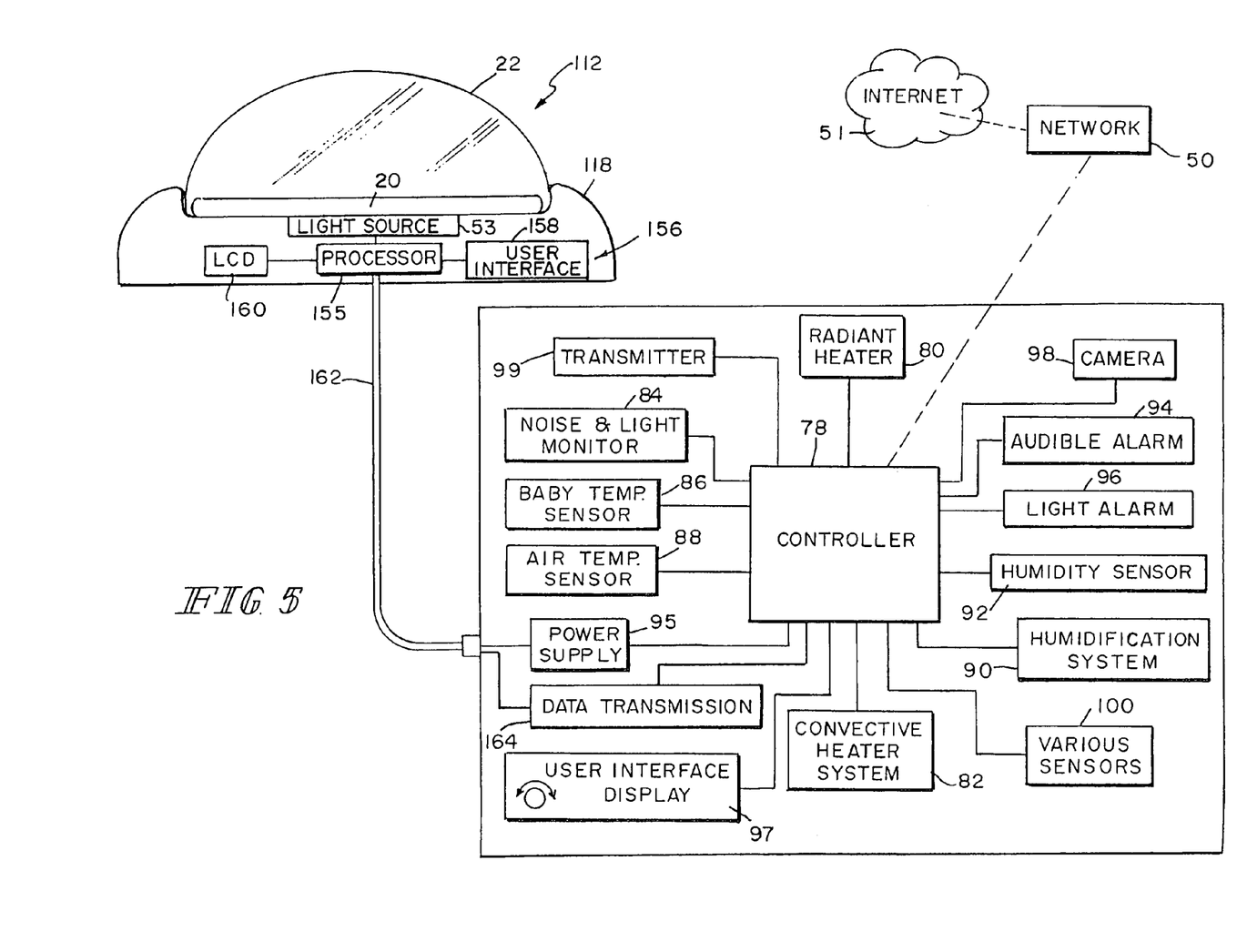
FIG. 5 is a diagrammatic view of another patient care apparatus having the incubator of FIG. 1 and another portable patient support module coupled to the incubator by a communication line, a controller of the incubator being in communication with a communication network adapted to communicate with the Internet.

Module 112 has circuitry 156 carried by platform 118, as illustrated in FIG. 5. Circuitry 156 has a user interface 158, a liquid crystal display 160, and a processor 155 coupled to interface 158 and LCD 160. Module 112 also has light source 53 coupled to processor 155 for providing phototherapy to infant 11. User interface 158 includes buttons that are pressed to scroll through data appearing on LCD 160 and to program system parameters, such as "on" and "off" times of light source 53. In some embodiments, user interface 158 controls the frequency with which camera 64 obtains a photo image of infant 11 and zooming of camera 64. In some embodiments, user interface 158 provides an alarm signal when the heart rate or respiratory rate of infant 11 is outside a desired range.

Module 112 and incubator 14 can communicate with one another by a communication line 162, as illustrated in FIG. 4. Line 162 is coupled to processor 155 and to a data transmission line 164 of incubator 14. Line 164 is in turn coupled to controller 78 of incubator so that processor 155 and controller 78 can communicate with one another. Controller 78 is couplable to communication network 50 which can connect to the Internet 51.

Platform 118 has an inner region 134 and an outer region 136 surrounding inner region 134, as illustrated in FIGS. 6 and 9-11. Inner region 134 is configured as a recessed mattress support deck for supporting mattress 20. Outer region 136 has four sides 145 which cooperate to provide an elevated rim 140 surrounding deck 134. In one embodiment (FIGS. 6, 9, and 10) of outer region 136, one of sides 145 has a notch 47 providing an opening 57 for receiving an x-ray tray 49 or a cassette of x-ray film into a space 148 underneath deck 134 and rim 140. X-rays can then be taken of infant 11 positioned on mattress 20 when removable components such as light source 53 and processor 155 are removed from a space 150 between upper 151 and lower 152 walls of deck 134. Deck 136 has support ribs 154 cooperating to maintain walls 151, 152 in spaced-apart relation to one another. Sides 145 cooperate to provide a foot 142 (FIGS. 9-10) extending under rim 140 to support module 112 on a surface 144. In another embodiment (FIG. 11) of outer region 136, none of sides 145 has notch 47 for x-ray tray 49 or a cassette of x-ray film.

Figure 6:
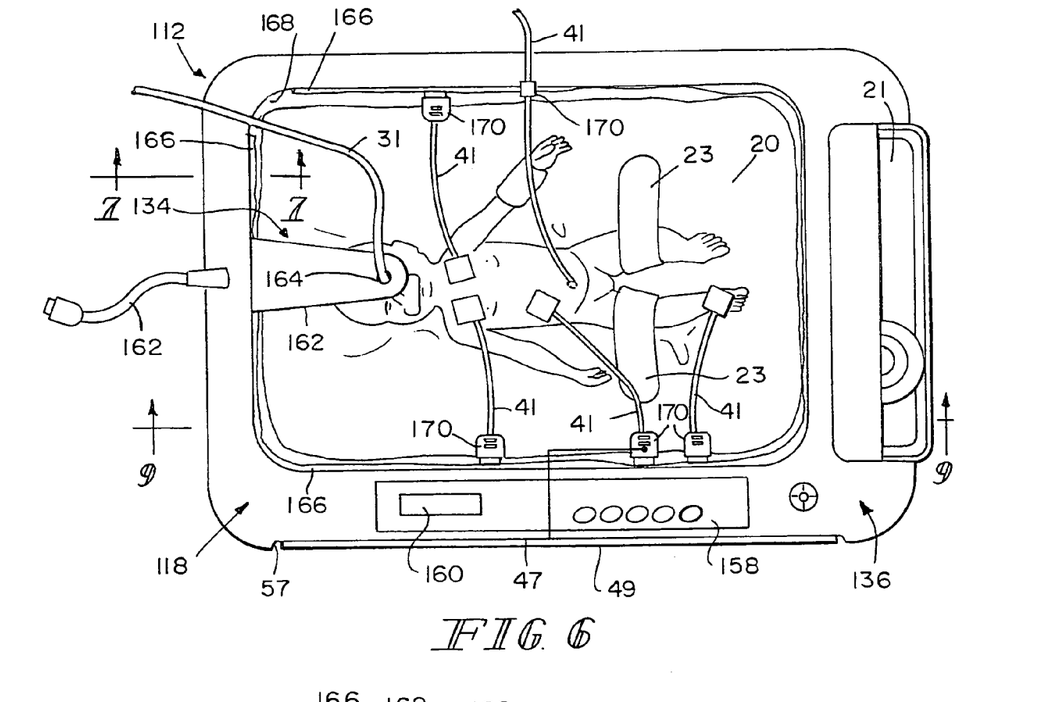
FIG. 6 is a top plan view of the portable patient support module of FIG. 5 showing the portable patient support module having line clips coupled to a rail for coupling infant care lines to a platform of the portable patient support module and a feeding line extending through an aperture formed in a canopy of the portable patient support module.
Figure 9:
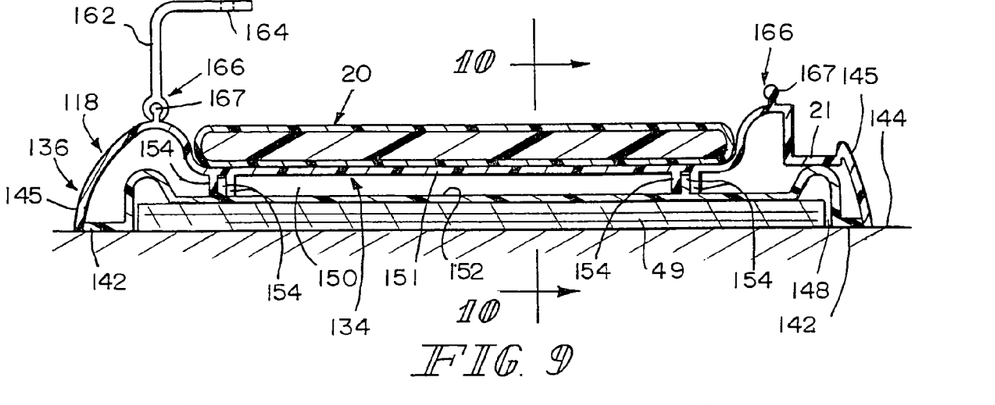
FIG. 9 is a sectional view taken along line 9-9 of FIG. 6 of the portable patient support module and an x-ray tray positioned thereunder, the rail having a member having a circular cross section.
Figure 11:
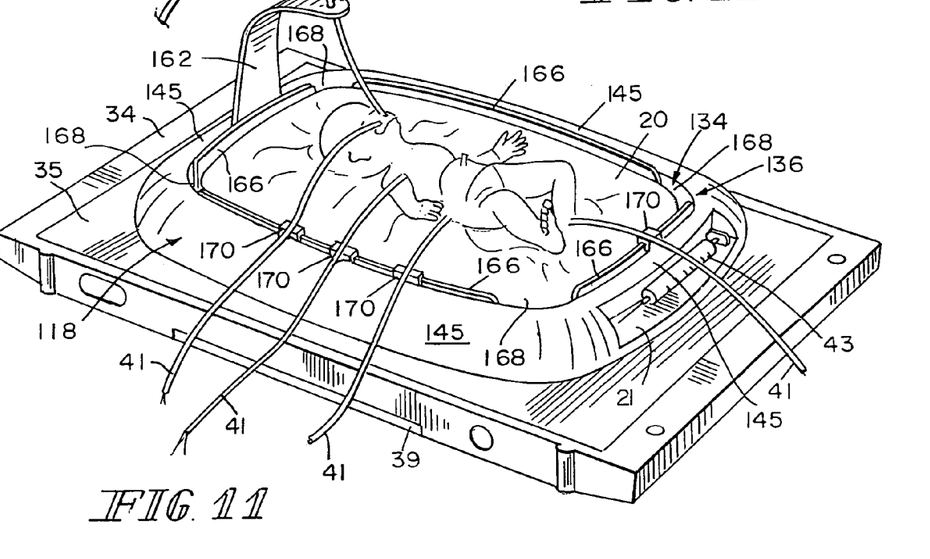
FIG. 11 is a perspective view of another portable patient support module having a platform with a rail and line clips coupled thereto.

A line holder 162 is coupled to and extends upwardly from one of sides 145, as illustrated in FIGS. 6, 9, and 11. Holder 162 has an aperture 164 through which feeding line 31 extends to maintain feeding line 31 in a desired position relative to infant 11.

Figure 7:
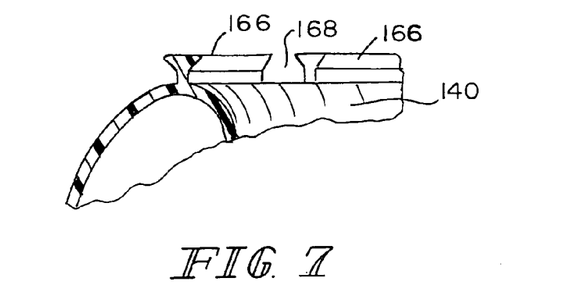
FIG. 7 is a sectional view taken along line 7-7 of FIG. 6 showing the rail having a dovetail-shaped cross section.
Figure 8:
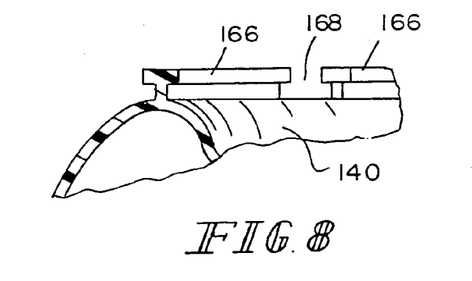
FIG. 8 is a view similar to FIG. 7 showing another rail having a T-shaped cross section.
Figure 10:
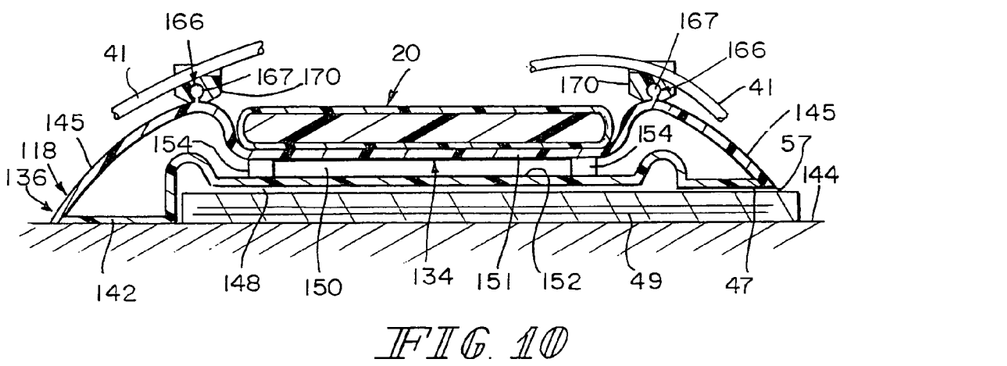
FIG. 10 is a sectional view taken along line 10-10 of FIG. 9.

A rail 166 is coupled to and extends upwardly from rim 140, as illustrated in FIGS. 6-8. Rail 166 has an opening 168 allowing one or more line clips 170 to be attached to and removed from rail 166. Clips 170 are configured to hold lines 41 and are slidable along rail 166 so that lines 41 can be positioned at desired locations around infant 11. Line holder 162 is also coupled to rail 166 for sliding movement along rail 166. Rail 166 has a member 167 having a circular cross section, as illustrated in FIGS. 9-10. In some embodiments, rail 166 has a dovetail-shaped cross section, as illustrated in FIG. 7. In other embodiments, rail 166 has a T-shaped cross section, as illustrated in FIG. 8.

In another embodiment of platform 118, platform 118 has a plurality of spaced-apart rails 166, one along each side 145, as illustrated in FIG. 11. Rails 166 are coupled to mattress support deck 134 at locations inwardly from rim 140. A number of clips 170 are coupled to and slidable along rails 166. Rails 166 have either a dovetail-shaped cross section, a T-shaped cross section, or a member 167 having a circular cross section. There are spaces 168 between adjacent rails 166 allowing clips 170 to be attached to and removed from rails 166.

A portable patient support module 212 (FIGS. 12-14) is similar to module 12 except as otherwise noted. Portable module 212 has a carrying platform 218, deformable, heat- and light-transmitting mattress 20 positioned on and carried by platform 218, and a removable canopy 222 positioned on and carried by platform 218. When canopy 222 is positioned on platform 218, canopy 222 and platform 218 cooperate to provide an enclosed infant isolation chamber 24 for isolating infant 11 positioned on mattress 20. The caregiver can carry portable module 212 by hand with infant 11 positioned in chamber 24 by holding onto platform 218.

Figure 12:
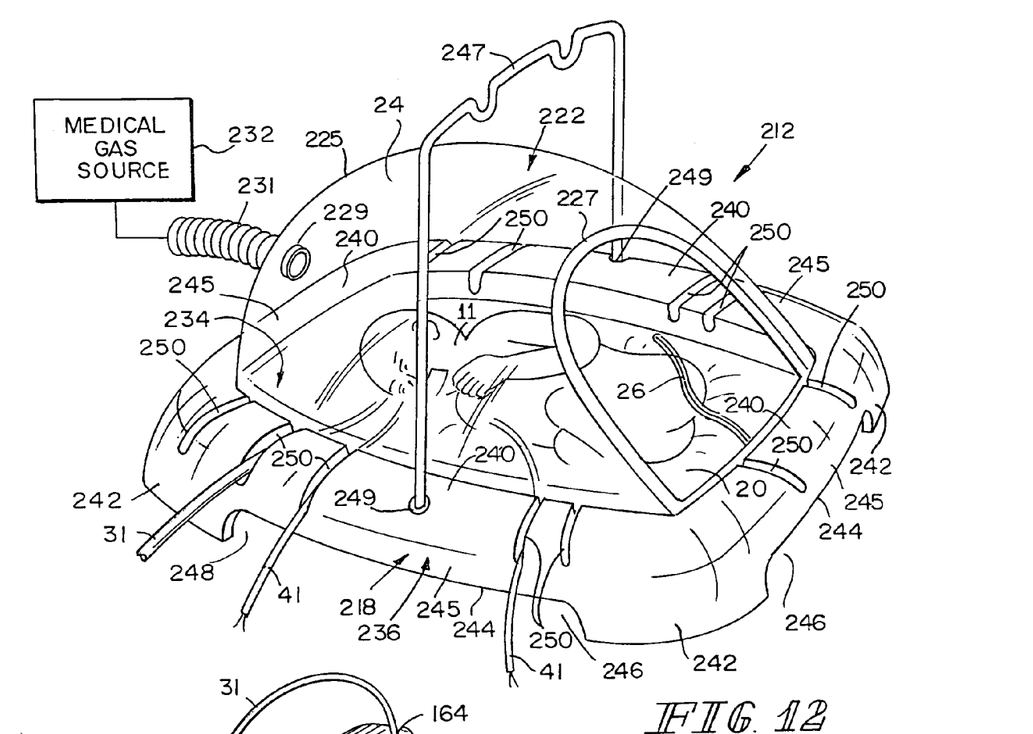
FIG. 12 is a perspective view of another portable patient support module having a platform formed to include grooves for receiving infant care lines.

Canopy 222 is made of generally transparent material allowing a caregiver to see infant 11 positioned in chamber 24 on mattress 20, as illustrated in FIG. 12. Canopy 222 has a domal portion 225 and an upwardly inclined annular planar portion 227 coupled to domal portion 225. Grommet 26 is coupled to and surrounded by planar portion 227. Domal portion 225 has an aperture 229 for receiving an infant care line or medical gas line 231 for introducing breathable medical gas, such as oxygen-enriched air, from a medical gas source 232 into chamber 24.

Figure 13:
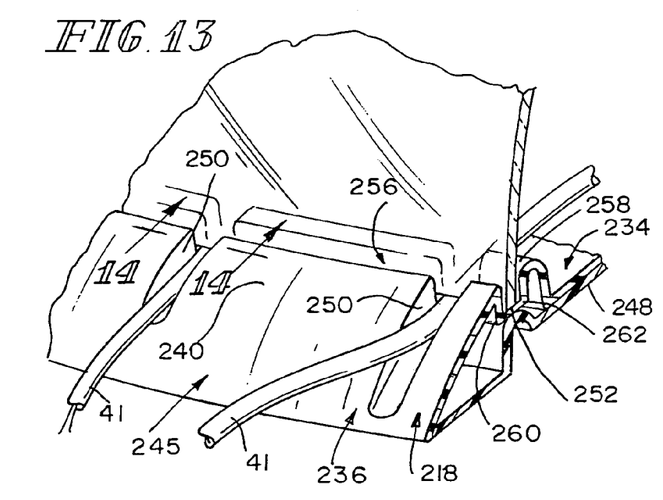
FIG. 13 is a fragmentary perspective view of the portable patient support module of FIG. 12 showing a pair of infant care lines extending through a pair of grooves formed in the platform and under a bottom edge of a canopy into an interior region.
Figure 14:
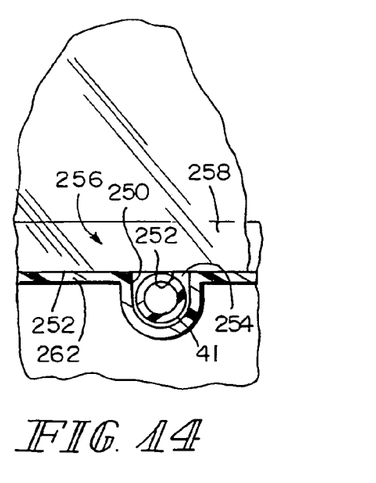
FIG. 14 is a sectional view taken along line 14-14 of FIG. 13 showing one of the infant care lines extending through one of the grooves formed in the platform.

Platform 218 has an inner region 234 and an outer region 236 surrounding inner region 234, as illustrated in FIGS. 12 and 13. Inner region 234 is configured as a recessed mattress support deck for supporting mattress 20. Outer region 236 has four sides 245 which cooperate to provide an elevated rim 240 surrounding deck 234. Sides 245 cooperate to provide four feet 242. Each side 245 has a notch 244 positioned between a pair of feet 242. Each notch 244 provides an opening 246 into a space 248 (FIG. 14) underneath rim 240 and deck 234 for receiving x-ray tray 49 or a cassette of x-ray film through opening 246 into space 248 allowing x-rays to be taken of infant 11 positioned on mattress 20. A gravage hanger 247 (FIG. 12) for supporting one or more infant care packages (not shown), for example, feeding bags, is mounted in a pair of hanger-receiving apertures 249 formed in outer region 236. Platform 218 a pair of hanger-receiving apertures 249 for mounting.

Rim 240 has a plurality of U-shaped line-receiving grooves 250 (FIGS. 12-14) for introducing a plurality of infant care lines 41 into isolation chamber 24 underneath a bottom edge 252 (FIGS. 13-14) of canopy 222. Each groove 250 and edge 252 cooperates to provide a passage 254 (FIG. 14) for the associated line 41. Rim 240 also has a canopy-receiving groove 256 (FIGS. 13-14) extending around rim 240 to receive edge 252. Line-receiving grooves 250 are transverse to canopy-receiving groove 256. Rim 240 has an inner wall 258, an outer wall 260, and a generally horizontal wall 262 extending therebetween. Walls 258, 260, 262 cooperate to provide groove 256 so that edge 252 rests on generally horizontal wall 262 between inner 258 and outer 260 walls. Line-receiving grooves 250 extend through walls 258, 260, 262.

Mattresses 20 and 35 need not be light transmissive, but can be of any mattress material, such as open celled foam or viscoelastic foam.

The term "lines" means conduits for carrying gases and/or liquids and electrical conductors for carrying signals.

In some embodiments, circuitry, for example, circuitry 56, 156, is housed in the internal space of platforms 18, 118, 218 in the outer regions (i.e., out board of the mattress footprint).

The invention claimed is:

1. A patient care apparatus comprising
a portable patient support module having a first mattress, a first platform carrying the first mattress, and a first canopy positioned on the first platform to enclose an infant positioned on the first mattress in a first isolation chamber, the portable patient support module being configured to be carried by hand when the infant is positioned on the first mattress, and
a second patient support module having a second mattress, a second platform carrying the second mattress, and a second canopy positioned on the second platform, the second platform and the second canopy cooperating to enclose the portable patient support module positioned on the second mattress in a second isolation chamber.

2. The patient care apparatus of claim 1, wherein the portable patient support module communicates with the second patient support module via a communication network.

3. The patient care apparatus of claim 2, wherein the portable patient support module and the second patient support module are coupled to the Internet via the communication network.

4. The patient care apparatus of claim 2, wherein the portable patient support module has circuitry coupled to the communication network, and the second patient support module has a controller coupled to the communication network.

5. The patient care apparatus of claim 1, further comprising a communication line coupled to the portable patient support module and the second patient support module.

6. The patient care apparatus of claim 5, wherein the portable patient support module has circuitry coupled to the communication line, and the second patient support module has a controller coupled to the communication line.

7. The patient care apparatus of claim 6, wherein the controller communicates with a communication network.

8. The patient care apparatus of claim 6, wherein the circuitry has a processor coupled to the communication line.

9. The patient care apparatus of claim 1, wherein the portable patient support module has a transmitter for wirelessly sending data relating to a physical condition of the infant, and further comprising a portable monitor for wirelessly receiving the data sent by the transmitter.

10. A patient care apparatus comprising
a mattress,
a platform carrying the mattress, the platform having a rail, and
a canopy positioned on the platform to enclose an infant positioned on the mattress,
a line clip for receiving a line associated with care of the infant, the line clip being coupled to the rail for movement along the rail; and
wherein the platform has a recessed mattress support deck receiving the mattress and a rim surrounding the recessed mattress support deck, and the rail extends upwardly from the recessed mattress support deck.

11. The patient care apparatus of claim 10, wherein the rail has a T shaped cross section for coupling the line clip to the rail.

12. The patient care apparatus of claim 10, wherein the rail has a dovetail-shaped cross section for coupling the line clip to the rail.

13. The patient care apparatus of claim 10, wherein the rail has a member having a circular cross section for coupling the line clip to the rail.

14. The patient care apparatus of claim 10, wherein the platform has a recessed mattress support deck receiving the mattress and a rim surrounding the recessed mattress support deck, and the rail extends upwardly from the rim.

15. The patient care apparatus of claim 10, wherein the platform has a tray for holding an item for treating the infant.

* * * * *